(12) United States Patent
Guerrero et al.

(10) Patent No.: US 7,601,483 B2
(45) Date of Patent: Oct. 13, 2009

(54) ANTI-REFLECTIVE COATINGS USING VINYL ETHER CROSSLINKERS

(75) Inventors: Douglas J. Guerrero, Rolla, MO (US); Robert Christian Cox, Rolla, MO (US); Marc W. Weimer, Rolla, MO (US)

(73) Assignee: Brewer Science Inc., Rolla, MO (US)

( * ) Notice: Subject to any disclaimer, the term of this patent is extended or adjusted under 35 U.S.C. 154(b) by 0 days.

(21) Appl. No.: 11/613,704

(22) Filed: Dec. 20, 2006

(65) Prior Publication Data

US 2007/0117049 A1 May 24, 2007

Related U.S. Application Data

(63) Continuation of application No. 11/105,862, filed on Apr. 14, 2005, now abandoned.

(60) Provisional application No. 60/566,329, filed on Apr. 29, 2004.

(51) Int. Cl.
*G03F 7/38* (2006.01)
*G03F 7/11* (2006.01)

(52) U.S. Cl. .............. 430/311; 430/326; 430/330; 430/325; 430/271.1; 430/272.1; 430/276.1; 430/275.1; 438/952; 438/761; 522/149

(58) Field of Classification Search ............... None
See application file for complete search history.

(56) References Cited

U.S. PATENT DOCUMENTS

| | | | |
|---|---|---|---|
| 3,345,210 A * | 10/1967 | Wilson | 427/102 |
| 3,561,962 A * | 2/1971 | Ewing | 430/290 |
| 3,615,615 A | 10/1971 | Lincoln et al | |
| 3,629,036 A * | 12/1971 | Isaacson | 430/256 |
| 3,682,641 A * | 8/1972 | Casler | 430/325 |
| 3,833,374 A * | 9/1974 | Patrick | 430/293 |
| 3,856,751 A | 12/1974 | Wilson | |
| 3,873,361 A * | 3/1975 | Franco et al. | 430/324 |
| 3,894,163 A * | 7/1975 | Broyde | 430/314 |
| 3,976,524 A * | 8/1976 | Feng | 438/424 |
| 4,137,365 A | 1/1979 | Fletcher et al. | |
| 4,175,175 A | 11/1979 | Johnson et al. | |
| 4,244,799 A | 1/1981 | Fraser et al. | |
| 4,320,224 A | 3/1982 | Rose et al. | |
| 4,346,163 A | 8/1982 | Takeyama et al. | |
| 4,369,090 A | 1/1983 | Wilson et al. | |
| 4,397,722 A | 8/1983 | Haller | |
| 4,430,419 A * | 2/1984 | Harada | 430/327 |
| 4,526,856 A * | 7/1985 | Lewis et al. | 430/191 |
| 4,578,328 A * | 3/1986 | Kray | 430/18 |
| 4,647,517 A * | 3/1987 | Hersener et al. | 430/321 |
| 4,683,024 A | 7/1987 | Miller et al. | |
| 4,732,841 A | 3/1988 | Radigan | |
| 4,738,916 A | 4/1988 | Namatsu et al. | |
| 4,742,152 A | 5/1988 | Scola | |
| 4,803,147 A | 2/1989 | Mueller et al. | |
| 4,808,513 A * | 2/1989 | Lazarus et al. | 430/331 |
| 4,845,265 A * | 7/1989 | Lapin et al. | 560/84 |
| 4,891,303 A | 1/1990 | Garza et al. | |
| 4,910,122 A | 3/1990 | Arnold et al. | |
| 4,927,736 A | 5/1990 | Mueller et al. | |
| 4,996,247 A | 2/1991 | Nelson et al. | |
| 5,057,399 A | 10/1991 | Flaim et al. | |
| 5,066,566 A * | 11/1991 | Novembre | 430/323 |
| 5,089,593 A | 2/1992 | Fjare et al. | |
| 5,091,047 A | 2/1992 | Cleeves et al. | |
| 5,106,718 A | 4/1992 | Bartmann et al. | |
| 5,126,231 A | 6/1992 | Levy | |
| 5,137,780 A | 8/1992 | Nichols et al. | |
| 5,169,494 A | 12/1992 | Hashimoto et al. | |
| 5,198,153 A | 3/1993 | Angelopoulos et al. | |
| 5,246,782 A | 9/1993 | Kennedy et al. | |
| 5,302,548 A | 4/1994 | Watanabe et al. | |
| 5,304,626 A | 4/1994 | Burgess et al. | |
| 5,336,925 A | 8/1994 | Moss et al. | |
| 5,340,684 A | 8/1994 | Hayase et al. | |
| 5,370,969 A | 12/1994 | Vidusek | |
| 5,397,684 A | 3/1995 | Hogan et al. | |
| 5,403,438 A | 4/1995 | Motoyama | |

(Continued)

FOREIGN PATENT DOCUMENTS

EP 1 033 624 A1 6/2000

(Continued)

OTHER PUBLICATIONS

Kansai Paint Co Ltd, English translation of JP 06295064 A from Patent Abstracts of Japan, http://www.ipdl.ncipi.go.jp/homepg_e.ipdl and Abstract in English.*

(Continued)

*Primary Examiner*—Cynthia Hamilton
(74) *Attorney, Agent, or Firm*—Hovey Williams LLP

(57) ABSTRACT

Novel, wet developable anti-reflective coating compositions and methods of using those compositions are provided. The compositions comprise a polymer and/or oligomer having acid functional groups and dissolved in a solvent system along with a crosslinker and a photoacid generator. The preferred acid functional group is a carboxylic acid, while the preferred crosslinker is a vinyl ether crosslinker. In use, the compositions are applied to a substrate and thermally crosslinked. Upon exposure to light, the cured compositions will decrosslink, rendering them soluble in typical photoresist developing solutions (e.g., alkaline developers).

29 Claims, No Drawings

U.S. PATENT DOCUMENTS

| | | | |
|---|---|---|---|
| 5,443,941 A | 8/1995 | Bariya et al. | |
| 5,542,971 A | 8/1996 | Auslander et al. | |
| 5,545,588 A | 8/1996 | Yoo | |
| 5,554,473 A | 9/1996 | Cais et al. | |
| 5,607,824 A | 3/1997 | Fahey et al. | |
| 5,632,910 A | 5/1997 | Nagayama et al. | |
| 5,633,210 A | 5/1997 | Yang et al. | |
| 5,688,987 A | 11/1997 | Meador et al. | |
| 5,691,101 A | 11/1997 | Ushirogouchi et al. | |
| 5,739,254 A | 4/1998 | Fuller et al. | |
| 5,772,925 A | 6/1998 | Watanabe et al. | |
| 5,807,790 A | 9/1998 | Gupta et al. | |
| 5,892,096 A | 4/1999 | Meador et al. | |
| 5,922,503 A | 7/1999 | Spak et al. | |
| 5,925,578 A | 7/1999 | Bae | |
| 5,939,235 A * | 8/1999 | Kondo et al. | 430/270.1 |
| 5,952,448 A | 9/1999 | Lee et al. | |
| 5,968,324 A | 10/1999 | Cheung et al. | |
| 5,972,560 A * | 10/1999 | Kaneko et al. | 430/270.1 |
| 5,998,569 A | 12/1999 | Hogan et al. | |
| 6,015,650 A | 1/2000 | Bae | |
| 6,020,269 A | 2/2000 | Wang et al. | |
| 6,042,997 A | 3/2000 | Barclay et al. | |
| 6,046,112 A | 4/2000 | Wang | |
| 6,054,254 A | 4/2000 | Sato et al. | |
| 6,063,547 A | 5/2000 | Ye et al. | |
| 6,071,662 A | 6/2000 | Carmichael et al. | |
| 6,103,456 A | 8/2000 | Tobben et al. | |
| 6,110,653 A | 8/2000 | Holmes et al. | |
| 6,121,098 A | 9/2000 | Strobl | |
| 6,124,077 A * | 9/2000 | Imai et al. | 430/281.1 |
| 6,127,070 A | 10/2000 | Yang et al. | |
| 6,136,511 A | 10/2000 | Reinberg et al. | |
| 6,136,679 A | 10/2000 | Yu et al. | |
| 6,156,658 A | 12/2000 | Wang et al. | |
| 6,156,665 A | 12/2000 | Hamm et al. | |
| 6,162,580 A | 12/2000 | Matsuoka et al. | |
| 6,165,695 A | 12/2000 | Yang et al. | |
| 6,171,763 B1 | 1/2001 | Wang et al. | |
| 6,187,509 B1 * | 2/2001 | Imai et al. | 430/284.1 |
| 6,200,907 B1 | 3/2001 | Wang et al. | |
| 6,207,238 B1 | 3/2001 | Affinito | |
| 6,218,292 B1 | 4/2001 | Foote | |
| 6,232,386 B1 | 5/2001 | Vargo et al. | |
| 6,251,562 B1 | 6/2001 | Breyta et al. | |
| 6,268,108 B1 | 7/2001 | Iguchi et al. | |
| 6,268,282 B1 | 7/2001 | Sandhu et al. | |
| 6,306,560 B1 | 10/2001 | Wang et al. | |
| 6,309,789 B1 | 10/2001 | Takano et al. | |
| 6,309,926 B1 | 10/2001 | Bell et al. | |
| 6,309,955 B1 | 10/2001 | Subramanian et al. | |
| 6,316,165 B1 | 11/2001 | Pavelchek et al. | |
| 6,319,649 B1 | 11/2001 | Kato et al. | |
| 6,319,651 B1 | 11/2001 | Holmes et al. | |
| 6,338,936 B1 | 1/2002 | Ichikawa et al. | |
| 6,359,028 B1 | 3/2002 | Miya et al. | |
| 6,361,833 B1 | 3/2002 | Nakada et al. | |
| 6,380,611 B1 | 4/2002 | Yin et al. | |
| 6,391,472 B1 | 5/2002 | Lamb | |
| 6,410,209 B1 | 6/2002 | Adams et al. | |
| 6,426,125 B1 | 7/2002 | Yang et al. | |
| 6,428,894 B1 | 8/2002 | Babich et al. | |
| 6,440,640 B1 | 8/2002 | Yang et al. | |
| 6,451,498 B1 | 9/2002 | Pirri et al. | |
| 6,455,416 B1 | 9/2002 | Subramanian et al. | |
| 6,458,509 B1 | 10/2002 | Haruta | |
| 6,458,705 B1 | 10/2002 | Hung et al. | |
| 6,487,879 B1 | 12/2002 | Blackwell et al. | |
| 6,488,509 B1 | 12/2002 | Ho et al. | |
| 6,509,137 B1 | 1/2003 | Wang et al. | |
| 6,558,819 B1 | 5/2003 | Igarashi | |
| 6,576,409 B2 | 6/2003 | Ichikawa et al. | |
| 6,586,560 B1 | 7/2003 | Chen et al. | |
| 6,602,652 B2 | 8/2003 | Adams et al. | |
| 6,616,692 B1 | 9/2003 | Glick et al. | |
| 6,638,853 B1 | 10/2003 | Sue et al. | |
| 6,680,252 B2 | 1/2004 | Chen et al. | |
| 6,709,979 B2 | 3/2004 | Komai et al. | |
| 6,740,469 B2 | 5/2004 | Krishnamurthy et al. | |
| 6,767,689 B2 | 7/2004 | Pavelchek et al. | |
| 6,803,168 B1 | 10/2004 | Padmanaban et al. | |
| 6,803,172 B2 | 10/2004 | Jung et al. | |
| 6,838,223 B2 | 1/2005 | Yoon et al. | |
| 6,844,131 B2 | 1/2005 | Oberlander et al. | |
| 6,846,612 B2 | 1/2005 | Deshpande | |
| 6,849,293 B2 | 2/2005 | Rawat | |
| 6,852,474 B2 | 2/2005 | Sabnis | |
| 6,872,506 B2 | 3/2005 | Neef et al. | |
| 6,893,702 B2 | 5/2005 | Takahashi | |
| 6,924,228 B2 | 8/2005 | Kim et al. | |
| 6,976,904 B2 | 12/2005 | Li et al. | |
| 7,074,527 B2 | 7/2006 | Lu et al. | |
| 7,265,431 B2 | 9/2007 | Sivakumar | |
| 2002/0009599 A1 | 1/2002 | Welch et al. | |
| 2002/0031729 A1 | 3/2002 | Trefonas, III et al. | |
| 2002/0045130 A1 | 4/2002 | Nitta et al. | |
| 2002/0076642 A1 | 6/2002 | Zampini et al. | |
| 2002/0106898 A1 * | 8/2002 | Tsai | 438/691 |
| 2002/0110665 A1 | 8/2002 | Rutter, Jr. et al. | |
| 2002/0120070 A1 | 8/2002 | Hong et al. | |
| 2002/0120091 A1 | 8/2002 | Scott | |
| 2002/0160211 A1 | 10/2002 | Kurita et al. | |
| 2002/0182874 A1 * | 12/2002 | Wang | 438/706 |
| 2002/0183426 A1 | 12/2002 | Lamb et al. | |
| 2003/0017688 A1 * | 1/2003 | Hsu et al. | 438/593 |
| 2003/0040179 A1 | 2/2003 | Thakar et al. | |
| 2003/0049566 A1 | 3/2003 | Sabnis et al. | |
| 2003/0064608 A1 | 4/2003 | Sabnis et al. | |
| 2003/0122269 A1 | 7/2003 | Weber et al. | |
| 2003/0129531 A1 | 7/2003 | Oberlander et al. | |
| 2003/0129547 A1 | 7/2003 | Neisser et al. | |
| 2003/0143404 A1 | 7/2003 | Welch et al. | |
| 2003/0162120 A1 * | 8/2003 | Yoon et al. | 430/156 |
| 2003/0166828 A1 | 9/2003 | Cox et al. | |
| 2003/0194636 A1 | 10/2003 | Wanat et al. | |
| 2003/0215736 A1 | 11/2003 | Oberlander et al. | |
| 2004/0010062 A1 | 1/2004 | Ahn et al. | |
| 2004/0018451 A1 | 1/2004 | Choi | |
| 2004/0058275 A1 | 3/2004 | Neef et al. | |
| 2004/0077173 A1 | 4/2004 | Sivakumar | |
| 2004/0210034 A1 | 10/2004 | Cox et al. | |
| 2004/0219456 A1 | 11/2004 | Guerrero et al. | |
| 2004/0220379 A1 | 11/2004 | Park et al. | |
| 2005/0074699 A1 | 4/2005 | Sun et al. | |
| 2005/0148170 A1 | 7/2005 | Bhave et al. | |
| 2005/0214674 A1 | 9/2005 | Sui et al. | |
| 2005/0255410 A1 | 11/2005 | Guerrero et al. | |
| 2006/0063106 A1 | 3/2006 | Cox et al. | |
| 2007/0196772 A1 | 8/2007 | Jung | |

FOREIGN PATENT DOCUMENTS

| | | |
|---|---|---|
| GB | 2 288 184 A | 11/1995 |
| JP | 48000891 | 1/1973 |
| JP | 06-295064 A | 10/1994 |
| JP | 06295064 A * | 10/1994 |
| JP | 08-062401 A | 3/1996 |
| JP | 10149531 | 6/1998 |
| JP | 10307394 A | 11/1998 |
| JP | 2003-162065 | 6/2003 |
| JP | 2003-183387 | 7/2003 |
| JP | 2005-70154 A | 3/2005 |
| KR | 10-2006-0028220 | 3/2006 |
| WO | WO 2004/001806 | 12/2003 |

| | | |
|---|---|---|
| WO | WO 2004/113417 A1 | 12/2004 |
| WO | WO 2005/111719 | 11/2005 |
| WO | WO 2005/111724 | 11/2005 |

OTHER PUBLICATIONS

White et al, "Synthesis and characterization of photodefinable polycarbonates for use as sacrificial materials in the fabrication of microfluidic devices" Proceedings of SPIE—vol. 4690 Advances in Resist Technology and Processing XIX, Theodore H. Fedynyshyn, Editor, Jul. 2002, pp. 242-253.*

Lee et al, Performance of vinyl ether cross-linkers on resist for 193 nm lithography, Advances in Resist Technology and Processing XIX,Proceedings of SPIE, vol. 4690, pp. 541-548, year 2000.*

"Synthesis and Characterizations of Photodefinable Polycarbonates for Use as Sacrificial Materials in the Fabrication of Microfludic Devices," White et al., School of Chemical Engineering, Georgia Institute of Technology, Atlanta, GA 30332-0100, Advances in Resist Technology and Processing XIX, Theodore H. Fedynyshyn, Editor, Proceedings of SPIE, vol. 4690 (2002), pp. 242-253.

"Removable Organic Antireflection Coating", Sturtevant et al., Advances in Resist Technology and Processing XIII, Roderick R. Kunz, Chair/Editor, SPIE, vol. 2724, pp. 738-746 (1996).

"Compatibility of Chemically Amplified Photoresists with Bottom Anti-Reflective Coatings," Yoshino et al., Advances in Resist Technology and Processing XV, Will Conley, Chair/Editor, SPIE, vol. 3333, pp. 655-661 (1998).

"Limits of Ultrathin Resist Processes," Okoroanyanwu, Future Fab Intl., Sep. 2003, pp. 1-15, http://www.future-fab.com/login.asp~s_id=0&d_ID=1158&login=true&mode=print.

Translated Abstract of JP Pub No.: JP 48000891, 1 page.

Translation of JP Pub No.: JP 10307394, 33 pages.

Translation of JP Pub No.: JP 10-149531, 17 pages.

Translation of JP Pub No.: JP 08-062401A, 7 pages.

Translated Abstract of JP No.: 2005-70154, 1 page.

Yamada et al., "Positive and Negative Tone Water Processable Photoresist: A Progress Report," SPIE vol. 3333, pp. 245-253 (1998).

Yamada et al., "The Design and Study of Aqueous-Processable Positive Tone Photoresists," SPIE vol. 3999. pp. 569-578 (2000).

Moon et al, "Three-Component Photopolymers Based on Thermal Cross-Linking and Acidolytic De-Cross-Linking of Vinyl Ether Groups. Effects of Binder Polymers on Photopolymer Characteristics," Chemistry of Materials, vol. 6, No. 10, Oct. 1994, pp. 1854-1860.

Translation of JP Pub No.: JP 06-295064, 16 pages.

Lee et al., "Performance of Vinyl Ether Cross-Linkers on Resist for 193 nm Lithography," SPIE vol. 4690, pp. 541-548 (2002).

"Aqueous Processable Positive and Negative Tone Photoresist," Wilson Research Group, University of Texas at Austin, Apr. 18, 2001, http://willson.cm.utexas.edu/Research/Sub_Files/Water_Soluble, 7 pages.

"Limits of Ultrathin Resist Processess," Okoroanyanwu, Future Fab Intl., Sep. 2003, pp. 1-15, http://www.future-fab.com/login.asp?s_id=0&d_ID=1158&login=true&mode=print.

Office Action dated Aug. 8, 2006, in U.S. Appl. No. 11/105,862.

Guerrero et al., "Photochemical Studies on Bottom Anti-Reflective Coatings," Journal of Photopolymer Science and Technology, vol. 19, No. 3, 2003, pp. 343-347.

Mack, "Antireflective Coatings," Microlithography World, Summer 1997, pp. 29-30.

Rubin et al., "Ion Implantation in Silicon Technology," American Institute of Physics, Jun./Jul. 2003, pp. 12-15.

Case Technology Inc., Ion Implantation, www.casetechnology.com/links.html, pp. 1-24, printed Aug. 2006.

2.2.3 Implantation Dose, www.iue.tuwien.ac.at/phd/hoessinger/node23.html, 1 page, printed Aug. 2006.

2.2.2 Ion Beam Energy, www.iue.tuwien.ac.at/phd/hoessinger/node22.html, 5 pages, printed Aug. 2006.

2.2.4 Tilt and Twist Angle, www.iue.tuwien.ac.at/phd/hoessinger/node24.html, 2 pages, printed Aug. 2006.

2.2 Ion Implantation Process Parameters, www.iue.tuwien.ac.at.phd/hoessinger/node20.html, 1 page, printed Aug. 2006.

2.2.1 Dopant Species, www.iue.tuwien.ac.at/phd/hoessinger/node21.html, 2 pages, printed Aug. 2006.

Ion Implantation Process, p2library.nfesc.navy.mil/P2_Opportunity_Handbook/1_12.html, 6 pages, printed Aug. 2006.

Translation of JP Pub No. 2003-162065; Jan. 2008, 19 pages.

Okazaki Masaki et al., "Positive-Working Photosensitive Alkaline-Developable Polymide Precursor Based on Semi-Alicyclic Poly (amide acid), Vinyl Ether Crosslinker, and a Photoacid Generator," J. Photopolym Sci Technol, vol. 19, No. 2, p 277-280.

Translation of WO 2005/111724, 19 pages, printed Jun. 6, 2008.

Yamaoka et al., "Dual-mode Behavior of Vinyl Ether Functionalized Photoresist," Journal of Polymer Science and Technology, vol. 7, No. 3(1994) 533-536.

* cited by examiner

US 7,601,483 B2

ANTI-REFLECTIVE COATINGS USING VINYL ETHER CROSSLINKERS

RELATED APPLICATIONS

This application claims the priority benefit of a provisional application entitled ANTI-REFLECTIVE COATINGS USING VINYL ETHER CROSSLINKERS, Ser. No. 60/566,329, filed Apr. 29, 2004, incorporated by reference herein. This application is a continuation of U.S. patent application Ser. No. 11/105,862, now abandoned entitled ANTI-REFLECTIVE COATINGS USING VINYL ETHER CROSSLERS, and filed on Apr. 14, 2005, and incorporated by reference herein.

FEDERALLY SPONSORED RESEARCH/DEVELOPMENT PROGRAM

This invention was made with government support under contract number DASG60-01-C-0047 awarded by the U.S. Army Space and Missile Defense Command. The United States government has certain rights in the invention.

BACKGROUND OF THE INVENTION

1. Field of the Invention

The present invention is concerned with novel wet developable anti-reflective coating compositions and methods of using the same.

2. Description of the Prior Art

As feature sizes shrink to less than 110 nm, new and more advanced materials will be needed to achieve the goals set by the semiconductor industry. improvements in both photoresists and bottom anti-reflective coatings are needed to achieve high-resolution lithography targets. For example, resist thickness loss that occurs during the bottom anti-reflective coating and substrate etch steps becomes a critical issue because new resists are much thinner than older generation materials. While resist thickness is being reduced, bottom anti-reflective coating thickness is not expected to decrease at the same rate, which further complicates the problem of resist loss. A solution to this problem is to eliminate the bottom anti-reflective coating etch step by using a wet-developable bottom anti-reflective coating.

Wet-developable bottom anti-reflective coatings have typically utilized a polyamic acid soluble in alkaline media as a polymer binder, thus allowing the bottom anti-reflective coating to be removed when the resist is developed. These traditional wet-developable bottom anti-reflective coatings are rendered insoluble in resist solvents taking advantage of a thermally driven amic acid-to-imide conversion. This process works well, however, it has two limitations: (1) the bake temperature window can be narrow (less than 10° C.) where the bottom anti-reflective coating remains insoluble in organic solvents but soluble in alkaline developer; and (2) the wet-develop process is isotropic, meaning the bottom anti-reflective coating is removed vertically at the same rate as horizontally, which leads to undercutting of the resist lines. While this is not a problem with larger geometries (greater than 0.2 micron), it can easily lead to line lifting and line collapse at smaller line sizes.

SUMMARY OF THE INVENTION

The present invention overcomes the problems of prior art wet developable anti-reflective coatings by providing new wet developable compositions that are useful in the manufacture of microelectronic devices.

In more detail, the inventive compositions comprise a compound selected from the group consisting of polymers, oligomers, and mixtures thereof dissolved or dispersed in a solvent system. The compound is preferably present in the composition at a level of from about 0.5-10% by weight, preferably from about 0.5-5% by weight, and even more preferably from about 1-4% by weight, based upon the total weight of all ingredients in the composition taken as 100% by weight.

If the compound is a polymer, it is preferred that the average molecular weight be from about 1,000-100,000 Daltons, and more preferably from about 1,000-25,000 Daltons. Preferred polymers include those selected from the group consisting of aliphatic polymers, acrylates, methacrylates, polyesters, polycarbonates, novolaks, polyamic acids, and mixtures thereof.

If the compound is an oligomer, it is preferred that the molecular weight be from about 500-3,000 Daltons, and more preferably from about 500-1,500 Daltons. Preferred oligomers include substituted and unsubstantiated acrylates, moethacrylates, novolaks, isocyanurates, glycidyl ethers, and mixtures thereof.

Regardless of whether the compound is an oligomer or polymer, and regardless of the structure of the polymer backbone or oligomer core, it is preferred that the compound comprise an acid functional group. The acid group is preferably present in the compound at a level of at least about 5% by weight, preferably from about 5-90% by weight, and even more preferably from about 5-50% by weight, based upon the total weight of the compound taken as 100% by weight. Preferred acid groups are groups other than phenolics, such as carboxylic acids (—COOH).

Unlike prior art compositions, the acid group is preferably not protected by a protective group. That is, at least about 95%, preferably at least about 98%, and preferably about 100% of the acid groups are free of protective groups. A protective group is a group that prevents the acid from being reactive.

Because protective groups are not necessary with the present invention, it is also preferred that the compound is not acid-sensitive. An acid-sensitive polymer or oligomer is one that contains protective groups that are removed, decomposed, or otherwise converted in the presence of an acid.

In another embodiment, a combination of protected acid groups and unprotected acid groups could be utilized. n these embodiments, the molar ratio of protected acid groups to unprotected acid groups is from about 1:3 to about 3:1, and more preferably from about 1:2 to about 1:1.

It is also preferred that the inventive compositions comprise a chromophore (light attenuating compound or moiety). The chromophore can be bonded with the compound (either to a functional group on the compound or directly to the polymer backbone or oligomer core), or the chromophore can simply be physically mixed in the composition. The chromophore should be present in the composition at a level of from about 5-50% by weight, and preferably from about 20-40% by weight, based upon the total weight of the compound taken as 100% by weight. The chromophore is selected based upon the wavelength at which the compositions will be processed. For example, at wavelengths of 248 nm, preferred chromophores include naphthalenes (e.g., napthithoic acid methacrylate, 3,7-dihydroxynaphthoic acid), heterocyclic chromophores, carbazoles, antiracenes (e.g., 9-anthracene methyl methacrylate, 9-anthraceniecarboxylic acid), and functional moieties of the foregoing. At wavelengths of 193 nm, preferred chromophores include substituted and unsubstantiated phenyls, heterocyclic chromophores (egg, furan rings, thiophene rings), and functional moieties of the foregoing. The preferred inventive compositions will also include a crosslinker.

Preferred crosslinkers are vinyl ether crosslinkers. It is preferred that the vinyl ether crosslinkers be multi-functional, and more preferably tri- and tetra-functional.

Preferred vinyl ether crosslinkers have the formula

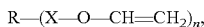

R—(X—O—CH=CH$_2$)$_n$, where R is selected from the group consisting of aryls (preferably $C_6$-$C_{12}$) and alkyls (preferably $C_1$-$C_{18}$, and more preferably $C_1$-$C_{10}$), each X is individually selected from the group consisting of: alkyls (preferably $C_1$-$C_{18}$, and more preferably $C_1$-$C_{10}$); alkoxys (preferably $C_1$-$C_{18}$, and more preferably $C_1$-$C_{10}$); carboxys; and combinations of two or more of the foregoing, and n is 2-6. The most preferred vinyl ether crosslinkers include those selected from the group consisting of ethylene glycol vinyl ether, trimethylolpropane trivinyl ether, 1,4-cyclohexane dimethanol divinyl ether, and mixtures thereof Another preferred vinyl ether crosslinker has a formula selected from the group consisting of

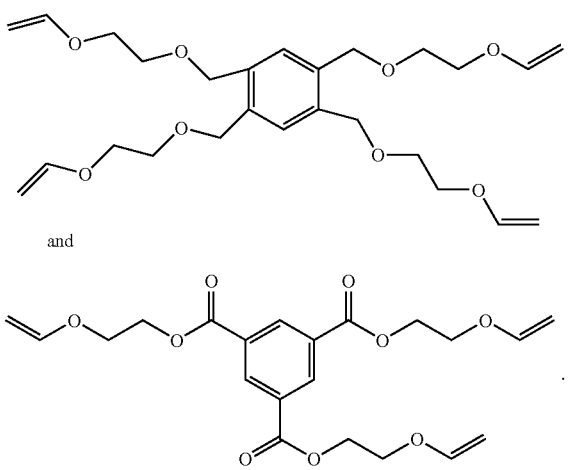

and

The preferred compositions also contain a catalyst. The preferred catalyst is an acid generator, and particularly a photoacid generator ("PAG," both ionic and/or non-ionic). Any PAG that produces an acid in the presence of light is suitable. Preferred PAGs include onium salts (e.g., triphenyl sulfonium perfluorosulfonates such as triphenyl sulfonium nonaflate and triphenyl sulfonium triflate), oxime-sulfonates (e.g., those sold under the name CGI® by CEBA), and triazines (e.g., TAZ108® available from Midori Kagaku Company).

The compositions preferably comprise from about 0.1-10% by weight of catalyst, and more preferably from about 1-5% by weight of catalyst, based upon the total weight of the polymer and oligomer solids in the composition taken as 100% by weight.

It will be appreciated that a number of other optional ingredients can be included in the compositions as well. Typical optional ingredients include surfactants, amine bases, and adhesion promoters.

Regardless of the embodiment, the anti-reflective compositions are formed by simply dispersing or dissolving the polymers, oligomers, or mixtures thereof in a suitable solvent system, preferably at ambient conditions and for a sufficient amount of the to form a substantially homogeneous dispersion, The other ingredients (e.g., crosslinker, PAG) are preferably dispersed or dissolved in the solvent system along with the compound.

Preferred solvent systems include a solvent selected from the group consisting of propylene glycol methyl ether acetate (PGMEA), propylene glycol methyl ether (PGME), propylene glycol n-propyl ether (PnP), ethyl lactate, and mixtures thereof. Preferably, the solvent system has a boiling point of from about 50-250° C., and more preferably from about 100-175° C. The solvent system should be utilized at a level of from about 80-99% by weight, and preferably from about 95-99% by weight, based upon the total weight of the composition taken as 100% by weight.

The method of applying the compositions to a substrate (such as a microelectronic substrate) simply comprises applying a quantity of a composition hereof to the substrate surface by any known application method (including spin-coating). The substrate can be any conventional circuit substrate, and suitable substrates can be planar or can include topography (e.g., contact or via holes, trenches). Exemplary substrates include silicon, aluminum, tungsten, tungsten silicide, gallium arsenide, germanium, tantalum, tantalum nitrite, SiGe, low k dielectric layers, dielectric layers (e.g., silicon oxide), and ion implant layers.

After the desired coverage is achieved, the resulting layer should be heated to a temperature of from about 100-250° C., and preferably from about 120-200° C., to induce crosslinking of the compound in the layer. In embodiments where the polymer or oligomer includes a carboxylic acid group, and the crosslinker is a vinyl ether crosslinker, the crosslinked polymers or oligomers will comprise acetal linkages having the formula

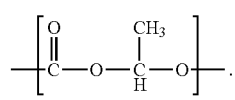

The crosslinked layer will be sufficiently crosslinked that it will be substantially insoluble in typical photoresist solvents.

Thus, when subjected to a stripping test, the inventive coating layers will have a percent stripping of less than about 5%, preferably less than about 1%, and even more preferably about 0%. The stripping test involves first determining the thickness (by taking the average of measurements at five different locations) of a cured layer. This is the average initial film thickness. Next, a solvent (e.g., ethyl lactate) is puddled onto the cured film for about 10 seconds, followed by spin drying at about 2,000-3,500 rpm for about 20-30 seconds to remove the solvent. The thickness is measured again at five different points on the wafer using ellipsometry, and the average of these measurements is determined. This is the average final film thickness.

The amount of stripping is the difference between the initial and final average film thicknesses. The percent stripping is:

$$\% \text{ stripping} = \left(\frac{\text{amount of stripping}}{\text{initial average film thickness}}\right) \times 100.$$

The crosslinked layers will also have superior light absorbance. The n value of this cured anti-reflective layer or coating will be at least about 1.3, and preferably from about 1.4-2.0, while the k value will be least about 0.1, and preferably from about 0.2-0.8, at the wavelength of use (e.g., 157 nm, 193 nm, 248 nm, 365 nm). The OD of the cured layers will be at least about 5/μm, preferably from about 5-15/μm, and even more preferably from about 10-15 μm, at the wavelength of use (e.g., 157 nm, 193 nm, 248 nm, 365 nm).

After the layers are cured, further steps can be carried out as necessary for the particular manufacturing process. For example, a photoresist can be applied to the cured layer and subsequently patterned by exposure to light of the appropriate wavelength followed by development of the exposed photoresist. Advantageously, as the photoresist is exposed to light, so is the inventive coating. Upon exposure to light, an acid is generated from the PAG, and this acid "decrosslinks" the compound in the layer. That is, the acid breaks the bond that was formed between the compound and the crosslinker upon thermal crosslinking. When a carboxylic acid is the acid group on the polymer or oligomer, decrosslinking results in the formation of the same polymer or oligomer originally present in the composition as well as an alcohol and an acetylaldehyde. This reaction is demonstrated in the scheme below (where R represents the polymer backbone or oligomer core, and RK represents the remainder of the vinyl ether crosslinker).

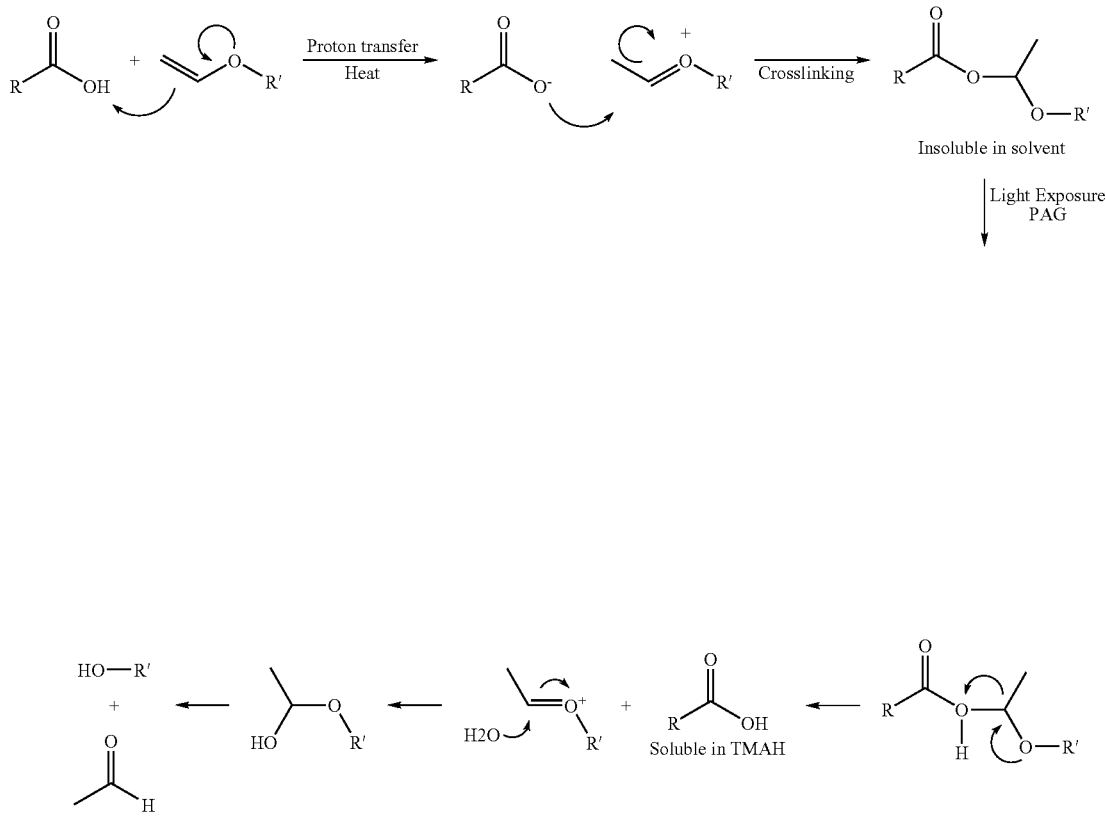

It will be appreciated that after this decrosslinking has occurred, the inventive coatings are rendered wet developable. That is, the cured compositions that have been exposed to light can be substantially (and preferable completely) removed with conventional aqueous developers such as tetramethyl ammonium hydroxide and KOH developers. Some of these developers are commercialized under the names PD523AD (available from JSR Micro), MF-319 (available from Shipley, Mass.), and NMD3 (available from TOK, Japan) developers. At least about 95%, preferably at least about 99%, and even more preferably 100% of the inventive coatings will be removed by a base developer such as tetramethyl ammonium hydroxide and/or KOH developers. This high percent solubility in commercially-available developers after light exposure is a significant advantage over the prior art as this shortens the manufacturing process and makes it less costly.

DETAILED DESCRIPTION OF THE PREFERRED EMBODIMENTS

The following examples set forth preferred methods in accordance with the invention. It is to be understood, however, that these examples are provided by way of illustration and nothing therein should be taken as a limitation upon the overall scope of the invention.

Materials and Methods

1. In-House Preparation of Tetrafunctional Vinyl Ether Crosslinker

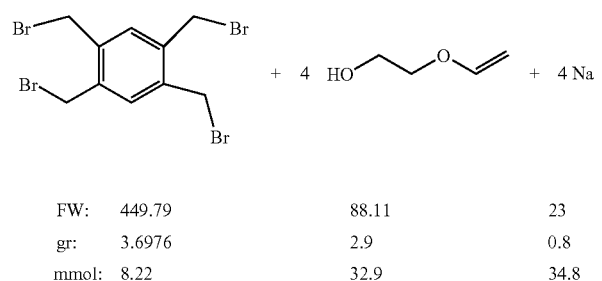

| FW: | 449.79 | 88.11 | 23 | 478.55 |
|---|---|---|---|---|
| gr: | 3.6976 | 2.9 | 0.8 | |
| mmol: | 8.22 | 32.9 | 34.8 | |

The reaction was carried out under $N_2$ in a 250-ml, 3-neck, round bottom flask. The Na cube was rinsed with hexane prior to use to remove mineral oil, placed quickly in a vial for weighing, and then transferred to the flask, which contained 50 ml THEF. An alcohol solution in THF (20 ml) was added dropwise through an addition funnel (about 15 minutes), and then heated to reflux until all of the Na was dissolved (about 30 minutes). The solution was light yellow and homogeneous. Tetrabromo drene dissolved in THF (15 ml) was added to the reaction flask dropwise (about 30 minutes), and allowed to reflux overnight. Upon addition, the mixture became heterogenious (NaBr precipitates).

After cooling, the salts were filtered and rinsed with TMF. The THF was removed in a rotary evaporator, and the remaining oil was redissolved in $CHC_3$ (25 ml). The chloroform solution was washed with water (2×25 ml), and then with brine (saturated NaCl, 25 ml). The organic layer was dried by passing it over a bed of silica gel. The solvent was removed. The product was left under vacuum for farther drying.

2. In-House Preparation of Trifunctional Vinyl Ether Crosslinker

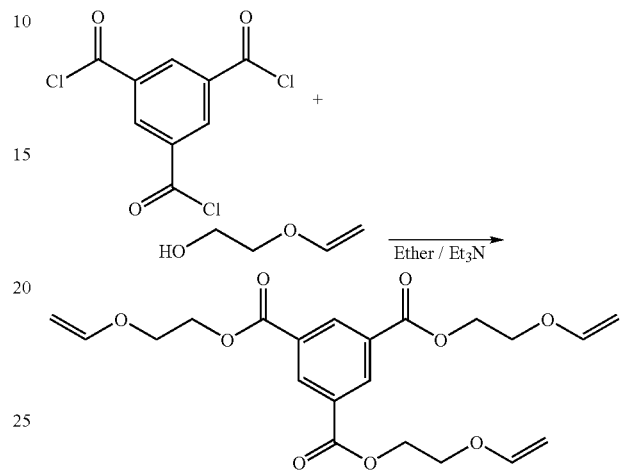

Ethylene glycol vinyl ether (6 grams) and triethyl amine (7.5 ml) were mixed in ether (40 ml) and treated dropwise with a solution of trimesic acid chloride (6 grams) in ether (40%). After addition, the mixture was heated to reflux for 1.5 hours. Residual salts were removed by filtration, and the ether

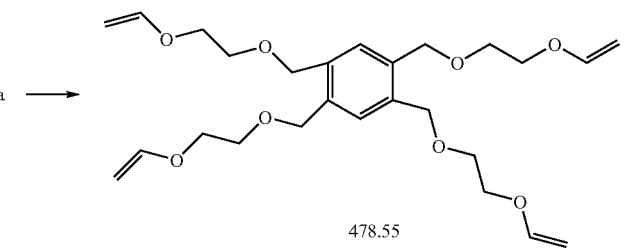

solution was washed with 10% NaOH (2×25 ml), washed with water (25 ml), and then dried over anhydrous magnesium sulfate. After removal of the solvent under pressure, light yellow oil was collected (69% yield).

EXAMPLE 1

Polymer Composition Without Acid Sensitive Groups

A homopolymer of methacryloyloxy ethyl phthalate (28.9 mmol, obtained from Aldrich) and 2,2'-azobisisobutyronitrile ("AIBN," 0.58 mmol radical initiator, obtained from Aldrich) were mixed in 50 ml tetrahydrofuran ("TEHF," obtained from Aldrich) under a nitrogen atmosphere and heated to reflux for 15 hours. The reaction was allowed to cool, concentrated to about 25 ml, and then precipitated into 200 ml hexane. After filtration and drying, about 8 grams of the remaining white powder were collected. The polymer molecular weight ("Mw") was measured by using polystyrene standards and gel permeation chromatography ("GPC") and was determined to be 68,400.

A 193-nm bottom anti-reflective coating was prepared as follows: A 3% solids formulation containing ethyl lactate ("EL," obtained from General Chemical), the polymer prepared above, 28% by weight Vectomer 5015 (a vinyl ether crosslinker obtained from Aldrich), and 4% by weight triphenyl sulfonium nonaflate (a PAG, obtained from Aldrich) was prepared and filtered through 0.1-micron endpoint filter. The crosslinker and PAG amounts were based on the weight of the polymer.

The above formulation was spin coated at 1,500 rpm on a silicon substrate and then baked at 160° C. The films were rinsed with EL to determine resistance to the resist solvent, exposed to light for 2 seconds, heated in a post-exposure bake ("PEB") at 130° C., and immersed in developer (tetramethylammonium hydroxide or "TMAH," sold under the name PD523AD, obtained from JSR Micro) for 60 seconds to decrosslink and remove the bottom anti-reflective coating. Table 1 below shows that the bottom anti-reflective coating had good solvent resistance, and that it could only be removed by an alkaline developer after exposure. This example shows that a polymer having an acid-sensitive group is not required for the crosslinking/decrosslinking process.

TABLE 1

| Initial Thickness (Å) | Thickness After 20 sec. EL Rinse (Å) | % Loss | Thickness After Development (No Exposure) (Å) | % Loss | Thickness After Exposure, PEB[a], and Development (Å) | % Loss |
|---|---|---|---|---|---|---|
| 619 | 590 | 4.7 | 712 | 0 | 65 | 90 |

[a]Post-exposure bake

EXAMPLE 2

Bottom Anti-Reflective Coating Containing Chromophore, Acid, and Dissolution Enhancer Methacrylic acid ("MAA," 31.2 mmol, obtained from Aldrich), tert-butyl methacrylate ("tBMA," 26.0 mmol, obtained from Aldrich), 9-anthracene methyl methacrylate ("9-AMMA," 14.5 mmol, obtained from St-Jean Photochemicals Sic.), and AIBN (1.4 mmol) were mixed in 60 ml THF under nitrogen atmosphere and heated to reflux for 19 hours. The reaction was allowed to cool, was concentrated to about 35 ml, and was then precipitated into 150 ml hexane. After filtration and drying, about 10 grams of a light yellow powder were collected. The polymer Mw, measured by using polystyrene standards and GPC, was determined to be 23,800.

A 3% solids formulation containing the polymer, PGME (obtained from General Chemical), PGMEA (obtained from General Chemical), 10% tetrafunctional vinyl ether crosslinker prepared in-house as described above, and 4% triphenyl sulfonium triflate (a PAG obtained from Aldrich) was prepared and filtered through a 0.1-micron endpoint filter. The crosslinker and PAG amounts were based on polymer weight. The above formulation was spin coated at 1,500 rpm onto a silicon substrate and then balked at 160° C. The optical constants at 248 nm were measured using a variable angle spectroscopic ellipsometer ("VASE") and were determined to be k=0.42 and n=1.4589. The film was rinsed with EL to test resistance to a resist solvent. After a rinse and spin dry cycle, no change in film thickness occurred. The cured film was immersed in 0.26 N TMAH solution, and no thickness loss occurred. However, after the film was exposed to light from a mercury-xenon lamp for 2 seconds and underwent a subsequent post-exposure bake at 130° C. for 90 seconds, the film became soluble in developer.

EXAMPLE 3

Control of Optical Properties by Polymer Composition

Several polymers were prepared using the procedure in Example 2 and using varying amounts of chromophore (9-AMMA) in order to demonstrate control of the optical properties of the bottom anti-reflective coating while maintaining dissolution properties. A 3% solids formulation containing POME, PGMEA, 10% tetrafunctional vinyl ether crosslinker prepared in-house as described above, and 4% triphenyl sulfonium triflate PAG was prepared and filtered through a 0.1-micron endpoint filter.

Table 2 shows that by increasing chromophore loading in the polymer, optical density, and substrate reflectivity can be controlled.

TABLE 2

| 9-AMMA (Mole %)[a] | k value | n value | OD/μm | 1st Minimum Thickness (Å) | Reflectivity at 1st Minimum Thickness (%) |
|---|---|---|---|---|---|
| 10 | 0.27 | 1.52 | 6.1 | 660 | 2.6 |
| 20 | 0.42 | 1.459 | 10.8 | 660 | 0.08 |
| 30 | 0.54 | 1.462 | 13.3 | 620 | 0.87 |

[a]based upon total moles of solids in composition

EXAMPLE 4

Comparative Example with Phenolic Polymer

A comparative example was prepared to demonstrate that vinyl ether crosslinking with a phenolic resin does not provide sufficient crosslinking density to prevent stripping by photoresist solvent.

In this procedure, 0.5 grams of polyhydroxystyrene ("PHS," obtained from DuPont), 0.02 grams of a triazine PAG (TAZ107, obtained from Midori Kagaku Company), 8.5 grams of EL, and various amounts of triscarboxyphenyl trivinyl ether prepared in-house were mixed and filtered through a 0.1-micron endpoint filter. Two additional formulations were also prepared in which 9-antiracene carboxylic acid ("9-ACA," a chromophore obtained from Aldrich) were added to the composition to form a bottom anti-reflective coating for 248-nm lithography. Films were spin coated onto silicon substrates and then baked at varying temperatures up to 205° C. Table 3 shows the results obtained. In all cases, the bottom anti-reflective coating stripped completely when rinsed with EL.

TABLE 3

| Polymer | Crosslinker:PHS Ratio | Bake Temperature (° C.) | PAG | Chromophore | EL Stripping (% change in film thickness) |
|---|---|---|---|---|---|
| PHS | 2:1 | 150, 205 | TAZ107 | — | 100 |
| PHS | 4:1 | 150, 205 | TAZ107 | — | 100 |
| PHS | 2:1 | 100-205[a] | TAZ107 | 9-ACA | 100 |
| PHS | 4:1 | 100-205 | TAZ107 | 9-ACA | 100 |

[a]tests were carried out at 10-degree intervals through this temperature range.

We claim:

1. A method of forming a microelectronic structure, said method comprising the steps of:
   providing a substrate having a surface;
   applying a composition to said surface, said composition comprising a compound dissolved or dispersed in a solvent system, said compound being selected from the group consisting of polymers, oligomers, and mixtures thereof, said compound comprising a carboxylic acid group;
   crosslinking the compound in said composition to form a layer of composition that is substantially insoluble in ethyl lactate and to yield crosslinked compounds comprising linkages having the formula

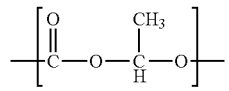

forming a photoresist layer on said composition; and
   exposing said composition to light so as to decrosslink said crosslinked compound.

2. The method of claim 1, wherein said crosslinking comprises thermally crosslinking said compound.

3. The method of claim 1, where said exposing step yields a layer of composition that is substantially soluble in photoresist developers selected from the group consisting of tetramethyl ammonium hydroxide, potassium hydroxide, and mixtures of the foregoing.

4. The method of claim 1, wherein said exposing step results in the breaking of the bond (*) of the linkage having the formula

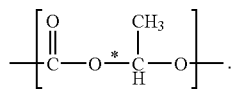

5. The method of claim 1, wherein said substrate is a microelectronic substrate.

6. The method of claim 5, wherein said substrate is selected from the group consisting of silicon, aluminum, tungsten, tungsten silicide, gallium arsenide, germanium, tantalum, tantalum nitrite, SiGe, ion implant layers, low k dielectric layers, and dielectric layers.

7. The method of claim 1, wherein:
   said substrate further comprises structure defining a hole, said structure including sidewalls and a bottom wall; and
   said applying step comprises applying the composition to at least a portion of said hole sidewalls and bottom wall.

8. The method of claim 1, wherein said substrate comprises an ion implant layer, and said applying step comprises forming a layer of said composition adjacent said ion implant layer.

9. The method of claim 1, wherein said compound is present in said composition at a level of from about 0.5-10% by weight, based upon the total weight of all ingredients in the composition taken as 100% by weight.

10. The method of claim 1, wherein said compound is not acid-sensitive.

11. The method of claim 1, wherein said carboxylic acid group is free of protective groups.

12. The method of claim 1, said composition further comprising a chromophore, wherein said chromophore is not bonded with said compound.

13. The method of claim 1, wherein said solvent system is utilized at a level of from about 95-99% by weight. based upon the total weight of the composition taken as 100% by weight.

14. The method of claim 1, said composition having a solids content of about 3%.

15. The method of claim 1, said composition further including a tetrafunctional vinyl ether crosslinking agent.

16. The method of claim 1, wherein during said applying said compound comprises protected acid groups and unprotected acid groups, wherein the molar ratio of protected acid groups to unprotected acid groups is from about 1:3 to about 3:1.

17. The method of claim 16, said compound comprising an acid group other than a phenolic group.

18. The method of claim 1, wherein during said applying at least about 95% of the carboxylic acid groups are free of protective groups.

19. The method of claim 1, said compound comprising an acid group other than a phenolic group.

20. A method of forming a microelectronic structure, said method comprising the steps of:
   providing a substrate having a surface, said substrate further comprising structure defining a hole, said structure including sidewalls and a bottom wall;

applying a composition to at least a portion of said hole sidewalls and bottom wall, said composition comprising a compound dissolved or dispersed in a solvent system, said compound being selected from the group consisting of polymers, oligomers, and mixtures thereof, said compound comprising a carboxylic acid group;

crosslinking the compound in said composition to yield crosslinked compounds comprising linkages having the formula

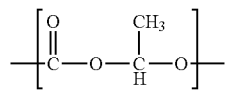

forming a photoresist layer on said composition; and exposing said composition to light so as to decrosslink said crosslinked compound.

21. The method of claim 20, said compound comprising an acid group other than a phenolic group.

22. A method of forming a microelectronic structure, said method comprising the steps of:

providing a substrate having a surface, said substrate comprising an ion implant layer;

applying a composition to said ion implant layer, said composition comprising a compound dissolved or dispersed in a solvent system, said compound being selected from the group consisting of polymers, oligomers, and mixtures thereof, said compound comprising a carboxylic acid group;

crosslinking the compound in said composition to yield crosslinked compounds comprising linkages having the formula

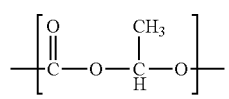

forming a photoresist layer on said composition; and exposing said composition to light so as to decrosslink said crosslinked compound.

23. The method of claim 22, said compound comprising an acid group other than a phenolic group.

24. A method of forming a microelectronic structure, said method comprising the steps of:

providing a substrate having a surface;

applying a composition to said surface, said composition comprising a compound dissolved or dispersed in a solvent system, said compound being selected from the group consisting of polymers, oligomers, and mixtures thereof, said compound comprising a carboxylic acid group that is free of protective groups;

crosslinking the compound in said composition to yield crosslinked compounds comprising linkages having the formula

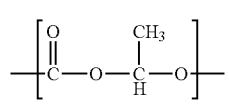

forming a photoresist layer on said composition; and exposing said composition to light so as to decrosslink said crosslinked compound.

25. The method of claim 24, said compound comprising an acid group other than a phenolic group.

26. A method of forming a microelectronic structure, said method comprising the steps of:

providing a substrate having a surface;

applying a composition to said surface, said composition comprising a compound dissolved or dispersed in a solvent system, said compound being selected from the group consisting of polymers, oligomers, and mixtures thereof, said compound comprising a carboxylic acid group, and said composition further comprising a chromophore, wherein said chromophore is not bonded with said compound;

crosslinking the compound in said composition to yield crosslinked compounds comprising linkages having the formula

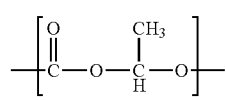

forming a photoresist layer on said composition; and exposing said composition to light so as to decrosslink said crosslinked compound.

27. The method of claim 26, said compound comprising an acid group other than a phenolic group.

28. A method of forming a microelectronic structure, said method comprising the steps of:

providing a substrate having a surface;

applying a composition to said surface, said composition comprising a compound dissolved or dispersed in a solvent system, said compound being selected from the group consisting of polymers, oligomers, and mixtures thereof said compound comprising a carboxylic acid group, said solvent system being present in said composition at a level of from about 95-99% by weight, based upon the total weight of the composition taken as 100% by weight;

crosslinking the compound in said composition to yield crosslinked compounds comprising linkages having the formula

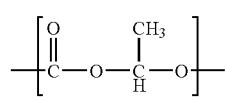

forming a photoresist layer on said composition; and exposing said composition to light so as to decrosslink said crosslinked compound.

29. A method of forming a microelectronic structure, said method comprising the steps of:
   providing a substrate having a surface;
   applying a composition to said surface, said composition comprising a compound dissolved or dispersed in a solvent system, said compound being selected from the group consisting of polymers, oligomers, and mixtures thereof, said compound comprising a carboxylic acid group, said composition having a solids content of about 3% by weight;
   crosslinking the compound in said composition to yield crosslinked compounds comprising linkages having the formula

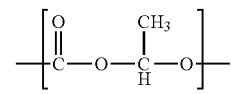

forming a photoresist layer on said composition; and
   exposing said composition to light so as to decrosslink said crosslinked compound.